(12) United States Patent
Mayer

(10) Patent No.: US 8,686,353 B2
(45) Date of Patent: Apr. 1, 2014

(54) APPARATUS SYSTEM AND METHOD FOR MASS ANALYSIS OF A SAMPLE

(75) Inventor: Thomas Mayer, Greensboro, NC (US)

(73) Assignee: Syngenta Crop Protection, LLC, Greensboro, NC (US)

( * ) Notice: Subject to any disclaimer, the term of this patent is extended or adjusted under 35 U.S.C. 154(b) by 467 days.

(21) Appl. No.: 12/863,045

(22) PCT Filed: Jan. 16, 2009

(86) PCT No.: PCT/US2009/031226
§ 371 (c)(1),
(2), (4) Date: Dec. 6, 2010

(87) PCT Pub. No.: WO2009/091961
PCT Pub. Date: Jul. 23, 2009

(65) Prior Publication Data
US 2011/0089318 A1    Apr. 21, 2011

Related U.S. Application Data

(60) Provisional application No. 61/021,365, filed on Jan. 16, 2008.

(51) Int. Cl.
*G01N 30/00* (2006.01)
(52) U.S. Cl.
USPC ............ 250/288; 250/281; 250/282; 250/283
(58) Field of Classification Search
USPC ................................................ 250/281–300
See application file for complete search history.

(56) References Cited

U.S. PATENT DOCUMENTS

| | | | | |
|---|---|---|---|---|
| 3,405,549 A * | 10/1968 | Finley | | 73/23.37 |
| 3,712,111 A * | 1/1973 | Llewellyn | | 73/23.37 |
| 4,377,745 A | 3/1983 | Chang | | |
| 5,668,373 A * | 9/1997 | Robbat et al. | | 250/339.12 |
| 6,066,848 A * | 5/2000 | Kassel et al. | | 250/288 |
| 6,147,346 A * | 11/2000 | Itoi | | 250/288 |
| 6,210,571 B1 * | 4/2001 | Zambias et al. | | 506/6 |
| 6,280,627 B1 * | 8/2001 | Kobayashi | | 210/656 |
| 6,637,263 B2 | 10/2003 | Zimmermann et al. | | |
| 6,817,554 B2 * | 11/2004 | Gangl et al. | | 239/696 |
| 6,841,774 B1 * | 1/2005 | Weiss | | 250/288 |
| 6,944,549 B2 | 9/2005 | McClure | | |
| 2002/0062680 A1 * | 5/2002 | Kikuchi et al. | | 73/23.42 |
| 2002/0108429 A1 * | 8/2002 | Kikuchi et al. | | 73/23.42 |
| 2003/0001090 A1 * | 1/2003 | Ranasinghe et al. | | 250/288 |
| 2003/0034407 A1 * | 2/2003 | Gangl et al. | | 239/690 |
| 2003/0136904 A1 * | 7/2003 | Mukaibatake | | 250/288 |
| 2003/0155497 A1 * | 8/2003 | Kato | | 250/281 |
| 2003/0224529 A1 * | 12/2003 | Maiefski et al. | | 436/173 |
| 2006/0054805 A1 * | 3/2006 | Flanagan et al. | | 250/288 |
| 2007/0000784 A1 | 1/2007 | Paul et al. | | |
| 2007/0113907 A1 * | 5/2007 | Brennen et al. | | 137/833 |
| 2008/0314129 A1 * | 12/2008 | Schultz et al. | | 73/61.55 |
| 2009/0165873 A1 * | 7/2009 | Chordia et al. | | 137/597 |

* cited by examiner

*Primary Examiner* — Michael Logie
(74) *Attorney, Agent, or Firm* — R. Kody Jones

(57) ABSTRACT

A mass spectrometer comprised of a mass analyzer, ion source and detector has the capability of analyzing samples in both positive and negative ionization modes. The mass spectrometer used in conjunction with a liquid chromatograph, fluid splitters and a plurality fluid pathways so that a large volume of analysis may be performed quickly and with high precision and accuracy. The apparatus is also capable of analyzing complex mixtures such as coeluting samples.

20 Claims, 1 Drawing Sheet

APPARATUS SYSTEM AND METHOD FOR MASS ANALYSIS OF A SAMPLE

This application is a 371 of International Application No. PCT/US2009/031226 filed Jan. 16, 2009, which claims priority to U.S. 61/021,365 filed Jan. 16, 2008, the contents of which are incorporated herein by reference.

BACKGROUND

Organic chemistry is a fundamental component to the advancement of technology and is central to the economic growth of many important industries such as plastics, fuel, pharmaceuticals, dyestuffs, and agrichemicals industries. A necessary component for the continued progress of chemistry is the evolution of the instruments and techniques for the synthesis, purification, characterization, and evaluation of organic compounds. Thus far, the improvements in instrumentation have revolutionalized organic chemistry, making it possible for chemists to refine the study of the delicate and complex structure of molecules and chemical reactions. These improvements have paved the way for the synthesis and development of a variety of compounds and molecules.

Since instrumentation plays a significant role in advancement of organic chemistry, many research and development facilities are equipped with the state-of-the-art equipment designed to allow the chemists to efficiently and accurately meet their project goals. Instruments such as mass spectrometers, nuclear magnetic resonance; gas and liquid chromatography; and infrared, ultraviolet, and visible spectroscopy are common types of sophisticated equipment found in these state-of-the-art laboratories.

Among these instruments, mass spectrometers provide a particularly useful tool for chemists because they are used to determine molecular weight, identify chemical structures, and accurately determine the composition of mixtures. As such, mass spectrometry (MS) is becoming increasingly important in biological research. For example, environmental scientists use mass spectrometers to identify organic chemicals in landfills, water supplies, and air samples. In the agrochemical industry, chemists quantitatively test samples for trace amounts of compounds to support water, soil, crop and animal studies.

Mass spectrometers generally have three basic components: an ionization source, a mass analyzer, and a detector system. When a sample molecule, or analyte, is first introduced into the mass spectrometer, it is received by the ionization source and bombarded with a beam of energetic electrons. Consequently, the analyte is broken apart into many ionized fragments. The mass analyzer component then sorts these ionized fragments by the ratio of their mass to electrical charge (m/z). A signal is then obtained and recorded by the detector system for each value of m/z that is represented, where the intensity of each signal reflects the relative abundance of the ion producing the signal. From this pattern of signals, the chemical structure of the analyte can be determined.

Mass spectrometers are oftentimes used in tandem with high performance liquid chromatography (HPLC) or gas chromatography instruments to determine the qualitative and quantitative properties of unknown substances. In other words, the chromatography instrument and the mass spectrometer are in fluid communication with one another. Accordingly, the sample is introduced into the chromatography instrument where it is separated into it components or analytes. Thereafter, the analytes are carried in-line to the mass spectrometer for analysis.

The spectral data generated from coupling high performance liquid chromatography and mass spectrometry yields various physical and chemical properties of the analyte tested, including the identification of an unknown analyte, its structure, and the amount present in the sample. As such, the combination of these instruments serves as a powerful analytical tool for analyzing complex samples. The agricultural industry and the pharmaceutical industry, in particular, have developed a reliance on this method, not only because of the type of data generated for the complex mixtures commonly tested, but also because these instruments are capable of providing the high sensitivity necessary to acquire accurate data at relatively quick analysis times.

As described, MS is an important technique and plays an instrumental role in the support and advancement of many industries, including the petroleum industry, pharmaceutical industry, and agrochemical industry. The demand for high-throughput analysis of compounds has spurred the introduction of new instrumentation and data management tools equipped to capture and archive analytical data and integrate the data into selected chemical and biological databases. Although the data generated with this technique is sound, there are various problems and challenges in keeping pace with this demand while maintaining accuracy and precision. For example, in a complex mixture, multiple analytical signals can overlap, masking a less intense analyte in the spectral data generated. In addition, it is difficult and time consuming to analyze large sets of data as numerous analyses need to be performed quickly with high precision and accuracy. The present invention is directed to an apparatus and method for meeting these needs.

BRIEF SUMMARY

The following apparatus and system, and aspects thereof are described and illustrated in conjunction with methods that are meant to be exemplary and illustrative, not limiting in scope. An apparatus is provided that is operative to receive a sample and analyze physical properties thereof. As disclosed, a mass analyzer, such as a mass spectrometer, broadly includes an inlet port communicating with the ionization source, and a plurality of fluid pathways in communication with the inlet port.

A first fluid pathway has a first construction and is adapted to receive and transfer the sample to the inlet port in a first time period. The second pathway has a second construction that is different from the first construction and is adapted to receive and transfer the sample to the inlet port in a second time period that is greater than the first time period. The second fluid pathway may be constructed, for example, to be greater in length than the first fluid pathway. Alternatively, the second fluid pathway may be smaller in diameter than the first fluid pathway. The fluid pathways may be formed of conventional tubing.

A first fluid splitter may be provided that is in communication with the first and second fluid pathways at a location upstream from the inlet port. The first fluid splitter is adapted to divide the sample into two portions wherein a first sample portion is directed to the first fluid pathway and the second sample portion is directed to the second fluid pathway. A second fluid splitter may also be used and located in spaced relation to the first fluid splitter and downstream thereof. The second fluid splitter interconnects the first and second pathways and directs the sample portions to a third fluid pathway prior to entry through the inlet port for analysis.

The fluid splitters used may be conventional splitters such as manuals splitters, electronic splitters, and T-splitters. The splitters used may also be adjustable. For example, the first fluid splitter may be operative to divide the sample in a ratio of 1:1 to 3:1.

Once received therein, the mass spectrometer may analyze the first sample portion in a first ionization mode. Thereafter, the mass spectrometer may be switched to analyze the second sample portion in a negative ionization mode. The first and second ionization modes may be selected from positive and negative ionization modes.

A system is further contemplated hereby. The system broadly includes a separatory column, such as HPLC, which is adapted to receive a sample and separate it into a plurality of analytes. Downstream of and in fluid communication with the separatory column is a mass spectrometric apparatus. The separatory column and mass spectrometer are interconnected by a plurality of pathways and a fluid splitter. The fluid splitter divides the analyte testing stream exiting the separator column into first and second testing portions, directing them down respective pathways prior to entry into the mass spectrometer. As with the apparatus described above, the system here can further be provided with a second fluid splitter adapted to direct the two testing portions through a common third fluid pathway prior to entry into the mass spectrometer. Also, as described above with respect to the apparatus, the first and second fluid pathways in the system are different in construction such that the first sample portion arrives at the inlet port in a first time period while the second sample portion arrives at a second time period.

The system may further be provided with a computer associated with both the separatory column and the mass spectrometric apparatus. The computer is operative to generate mass spectral data of both testing portions.

The apparatus and system described may have particular utility for analyzing samples, or testing portions, having coeluting analytes. In this way, the mass analyzing apparatus can analyze both portions in different ionization modes.

A method of analyzing a sample containing coeluting analytes is further contemplated. Broadly, the method includes dividing the sample into a first testing portion and a second testing portion and then directing the first and second testing portions toward the inlet port via two different fluid pathways to the mass analysis apparatus. The mass analysis apparatus performs an analysis on the first testing portion in a first ionization mode thereby to produce a first peak profile. The second testing portion, on the other hand, is directed to the inlet port of the mass analysis via a second fluid pathway and analyzed in a second ionization mode thereby to produce a second peak profile. Particularly, the mass analyzing apparatus analyzes one portion in the positive ionization mode while the other is analyzed in the negative ionization mode.

The method may further include the step of providing a separatory column at a location upstream from the mass analysis apparatus. Accordingly, the sample could be first directed through the separatory column, such as HPLC, thereby to separate the sample into a plurality of analytes. Thereafter, the analytes would travel downstream to the mass analysis apparatus.

The method could include the step of directing the first and second testing portions simultaneously to their respective pathways. The testing portions, should, however reach the inlet port at different time periods. For example, the first testing portion may be received by the inlet port in a first time period while the second testing portion arrives through the inlet port at a second time period that is greater than the first.

An exemplary embodiment is illustrated in the referenced figures of the drawings. It is intended that the embodiments and figures disclosed herein be considered illustrative rather than limiting. In the figures:

DETAILED DESCRIPTION

Corporate agribusiness and agrichemical companies are in the business of supporting agricultural needs by developing and manufacturing chemicals and genetically modified products for a sustainable agriculture that is environmentally and socially acceptable while at the same time, economically viable. As part of this goal, many agrichemical companies take an active role in safeguarding the environment. For example, many agrichemical companies monitor water bodies and community water supplies to test for certain chemicals and their concentrations.

Figure 1:
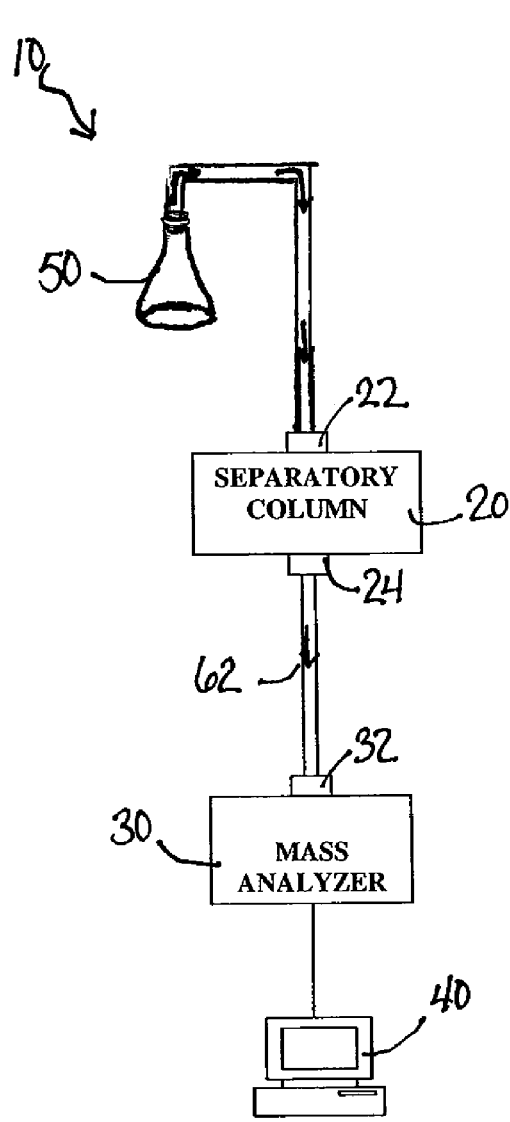
FIG. 1 is a schematic view showing a prior art system for analyzing samples that includes a mass analyzer in fluid communication with a separatory column.

Oftentimes, for example, water samples are collected from a selected water body and analyzed using a mass spectrometer in tandem with high performance liquid chromatography. Results of these analyses identify the chemical contaminants, if present, as well as the concentration of those contaminants. The conventional technique for analyzing water samples is generally illustrated in FIG. 1. Here, system 10 includes separatory column 20, which may be in the form of a conventional high performance liquid chromatography (HPLC) in fluid communication with mass analyzer 30, which may be a conventional mass spectrometer. HPLC 20 and mass spectrometer 30 are each associated with computer 40, which generates the mass spectral data evaluated by the chemist.

HPLC 20 has an inlet 22 to receive sample 50 and an outlet 24 through which the separated analytes exit the separatory column. Outlet 24 is in fluid communication with inlet port 32 of spectrometer 30, which communicates with the ionization source. With this structure in mind, the flow of the analysis sample follows the direction of the arrows and can be understood to first enter HPLC 20 through inlet 22 where it is separated into its analytes. These analytes form analyte stream 62, which flows from outlet 24 and through inlet port 32 into mass spectrometer 30. Conventional tubing of appropriate size and length interconnects HPLC 20 and mass spectrometer 30 and carries analyte stream 62 from outlet 24 to inlet port 32. This tubing may be, for example, polymer tubing, such as polyetheretherketone (PEEK) tubing, stainless steel tubing, or other appropriate tubing. Computer 40 then generates the spectral data for the analytes within the analyte stream.

Oftentimes, analytes will coelute from the HPLC. In other words, two different constituents within the sample will elute from the exit end of the column at approximately the same time. In the event that these coeluants have different polarities i.e. where one coeluting analyte is positive and the other coeluting analyte is negative, it becomes necessary to switch the polarity of the mass spectrometer in order for both analytes to be detected thereby. Accordingly, when the mass spectrometer is operated in a positive ionization mode, it will detect the positive coeluting analyte. Similarly, when the mass spectrometer is operated in the negative ionization mode, it will detect the negative coeluting analyte.

Currently, the process employed for analyzing coeluting analytes is to feed the analyte stream into the mass spectrometer, as described above with reference to FIG. 1, while it is operating in a first mode, either the positive or negative ionization mode. After the mass spectrometer has analyzed the analyte stream in the first mode, its polarity can then be switched into the second mode. The analyte stream is injected into the mass spectrometer a second time and analyzed. In this way, the computer will be able to generate the spectral data for both the positive and negative analytes.

Injecting the analyte stream through the mass spectrometer two different times can be time consuming, especially when there is a large volume of samples to analyze. For example, typical HPLC equipment can hold one hundred (100) samples to be analyzed. It usually takes approximately ten (10) minutes for one sample to elute from the HPLC and then be analyzed by the mass spectrometer one time. So, the time it takes for a set of 100 samples to be analyzed when the mass spectrometer is in a first mode (either positive or negative ionization mode) is approximately seventeen (17) hours. Chemists will typically place the same 100 samples in the HPLC and run the same analysis procedure a second time after switching the mass spectrometer into the second ionization mode. This second analysis takes another seventeen (17) hours for a total analysis time of approximately 34 hours.

Figure 2:
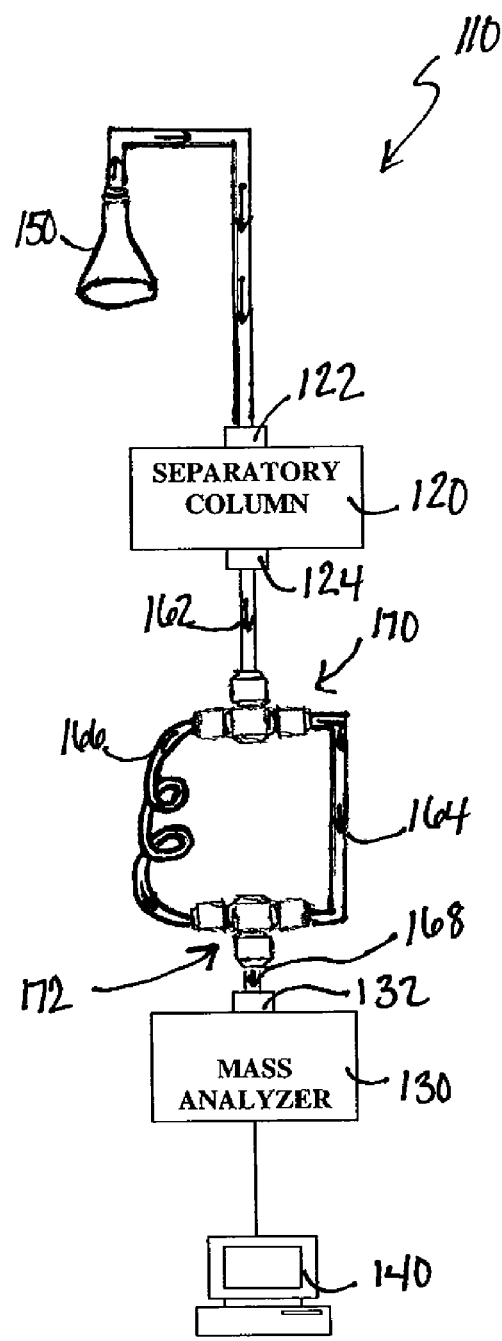
FIG. 2 is a schematic view showing an exemplary embodiment of an analysis system that includes a mass analyzer and a separatory column interconnected by a plurality of fluid pathways.

As will be appreciated, the mass spectrometer apparatus, system, and method described herein with reference to FIG. 2 can analyze the same 100 samples in far less time than the approximate thirty-four (34) hours described above. Similar to system 10 described above with reference to FIG. 1, system 110 shown in FIG. 2 includes separatory column 120, such as an HPLC, in fluid communication with mass analyzer 130, which may be a conventional mass spectrometer, associated with computer 140. Again, following the direction of the arrows, sample 150 is introduced into HPLC 120 via inlet 122 where it is separated into its analytes. Analyte stream 162 flows from HPLC 120 to mass spectrometer 130 for analysis, but before reaching the mass spectrometer, the stream is divided into two portions—a first testing portion and a second testing portion. Each testing portion reaches inlet port 132 separately such that first testing portion, for example, can be analyzed by the mass spectrometer before the second testing portion is introduced therein.

More particularly, and with continued reference to FIG. 2, analyte stream 162 exits HPLC 120 via outlet 124 and is transferred downstream to first fluid splitter 170. First fluid splitter 170 divides analyte stream 162 into a first testing portion and a second testing portion. The first testing portion is directed to first fluid pathway 164 having a first construction while the second testing portion is directed to second fluid pathway 166, which has a second construction that is different than the first construction. First and second fluid pathways 164, 166 are interconnected to third fluid pathway 168 by second fluid splitter 172. As shown here, second fluid splitter 172 is located downstream of first fluid splitter 170 at a location proximate to inlet port 132. Once the respective testing portions are received thereby, third fluid pathway 168 transfers the testing portions to mass spectrometer 130 via inlet pot 132.

First fluid pathway 164, second fluid pathway 166, and third fluid pathway 168 may each be formed of conventional tubing as described above. First fluid pathway 164 and second fluid pathway 166 are different in construction such that the respective testing portions received thereby ultimately flow through inlet port 132 at different times. As contemplated, the first testing portion enters the mass spectrometer in a first time period and analyzed in a first ionization mode. Then, the second testing portion enters the mass spectrometer in a second time period after sufficient time has lapsed for the analysis to complete on the first testing portion and for the mass spectrometer to be switched into the second ionization mode.

To further exemplify the efficiency of system 110, a hypothetical sample containing coeluting analytes is first introduced into separatory column 120. After approximately three (3) minutes, the analytes coelute forming analyte stream 162, which is subsequently divided by first fluid splitter 170. A first testing portion is directed down first fluid pathway 164 and reaches mass analyzer 130 after approximately three (3) minutes and ten (10) seconds. Meanwhile, the second testing portion flows down second fluid pathway 166 and arrives at mass spectrometer after approximately three (3) minutes and eleven (11) seconds. The ionization mode of standard mass spectrometer equipment can take less than a second. Accordingly, if it takes approximately ¾ second (750 ms) to switch the mass spectrometer between the first and second modes, the spectral data of the second testing portion can be analyzed so long as it is approximately one (1) second after the first testing portion.

The construction of fluid pathways 164, 166 can be constructed in any way appropriate to achieve the delivery of the testing portions in different time frames. For example, as shown here, second fluid pathway 166 looped over itself two times such that it is greater in length than that of first fluid pathway 164. Accordingly, it takes second testing portion longer to be received by the inlet port due to the length of pathway 166 than compared to the first testing portion. Alternatively, first fluid pathway 166 may be larger in diameter than second fluid pathway 164 such that the velocity of the second testing portion while traveling in the second fluid pathway is slower than that of the first testing portion.

The fluid splitters used in the system described may be conventional splitters oftentimes employed with analytical equipment. For example, the splitters may be manual splitters, electronic splitters, or T-splitters, to name a few. Additionally, the splitters may be adjustable or non-adjustable as desired. For example, first fluid splitter 170 may split analyte stream 162 in a ratio of 1:1, for example, or alternatively, in a ratio of 3:1. More particularly, the first fluid splitter may be an Upchurch P-450, manufactured by Upchurch Scientific, Inc. with offices located at 619 Oak Street Oak Harbor, Wash. 98277, and the second fluid splitter may be ASI Model 60206, offered by W. R. Grace & Co., with an office located at 2051 Waukagen Road, Deerfield, Ill. 60015. One or any combination of fluid splitters may be used, as appropriate, for directing the analyte stream via the pathways such that the testing portions enter the mass spectrometer in different time periods.

As should be readily appreciated by the ordinarily skill artisan, the utility of system 110 and the aspects thereof described above in reference to FIG. 2 can be used to test coeluting analytes for industries other than the agrichemical industry. Accordingly, the system and the aspects thereof may be useful in many industries, such that it is in no way intended to be limited to the agrichemical industry. For example, the pharmaceutical industry or other industries that analyze coeluting analytes could employ this system to improve the efficiency and time for testing the samples.

In addition, system 110 above was shown and described as including a mass analyzer in tandem a separatory column, specifically HPLC. The mass analyzer and its benefits can readily be appreciated if used in tandem with equipment other than HPLC as appropriate, for example, an ultra pressure liquid chromatography (UPLC). Alternatively, the mass analyzer and the plurality of fluid pathways that introduce the sample thereto could be used independently. In other words, the sample to be tested could be introduced directly into a fluid pathway and subsequently divided into first and second testing portions that are then introduced into the mass analyzer at different time periods sufficient to allow for an analysis of the sample to take place in different ionization modes.

A method of analyzing a sample containing coeluting analytes is further contemplated. It should be understood that the methodology may include any of the steps that are any of the steps inherent in the above-described embodiment of the apparatus and system. Broadly, though, the method includes dividing the sample into a first testing portion and a second testing portion and then directing the first and second testing portions toward the inlet port via two different fluid pathways to the mass analysis apparatus. The mass analysis apparatus performs an analysis on the first testing portion in a first ionization mode thereby to produce a first peak profile. The second testing portion, on the other hand, is directed to the inlet port of the mass analysis via a second fluid pathway and analyzed in a second ionization mode thereby to produce a second peak profile. Particularly, the mass analyzing apparatus analyzes one portion in the positive ionization mode while the other is analyzed in the negative ionization mode.

The method may further include the step of providing a separatory column at a location upstream from the mass analysis apparatus. Accordingly, the sample could be first directed through the separatory column, such as HPLC, thereby to separate the sample into a plurality of analytes. Thereafter, the analytes would travel downstream to the mass analysis apparatus.

As noted, the method may include any of the steps inherent in the above-described system or apparatus. Specifically, the method could include the step of directing the first and second testing portions simultaneously to their respective pathways. The testing portions, should, however reach the inlet port at different time periods. For example, the first testing portion may be received by the inlet port in a first time period while the second testing portion arrives through the inlet port at a second time period that is greater than the first.

The first and second fluid paths may be interconnected by a fluid splitter, which is also operative to divide the sample stream into the first and second testing portions. The construction of the fluid paths may also be different. For example the first fluid path may have a length that is greater than that of the second fluid path.

The foregoing description and the illustrative embodiment of the present invention have now been described in detail. It should be understood, however, that the foregoing description of the present invention is exemplary only, and that the scope of the present invention is to be limited to the claims as interpreted in view of the prior art. Moreover, the invention illustratively disclosed herein suitably may be practiced in the absence of any element which is not specifically disclosed herein.

I claim:

1. A mass spectrometer operative to receive a liquid sample and analyze physical properties thereof, said mass spectrometer having an ionization source, a mass analyzer, and a detector, comprising:
   (A) an inlet port communicating with the ionization source through which the sample is introduced for analysis;
   (B) a first fluid pathway in communication with the inlet port and having a first construction, said first fluid pathway adapted to receive and transfer the sample to the inlet port in a first time period;
   (C) a second fluid pathway in communication with the inlet port and having a second construction that is different than the first construction, said second fluid pathway adapted to receive and transfer the sample to the inlet port in a second time period that is greater than the first time period;
   (D) a first fluid splitter in communication with said first and second fluid pathways and located upstream from the inlet port, said first fluid splitter adapted to divide the sample into a first sample portion and a second sample portion such that said first sample portion is transferred to the inlet port via said first pathway and said second sample portion is transferred to the inlet port via said second pathway; and
   (E) a second fluid splitter located downstream from said first fluid splitter and interconnecting the first and second fluid pathways such that said first and second sample portions are received by the inlet port via a common fluid pathway.

2. A mass spectrometer according to claim 1 wherein said first fluid pathway is constructed to have a first length and said second fluid pathway is constructed to have a second length that is greater than the first length.

3. A mass spectrometer according to claim 1 wherein said first fluid pathway is constructed to have a first diameter and said second fluid pathway is constructed to have a second diameter that is smaller than the first diameter.

4. A mass spectrometer according to claim 1 wherein said first sample portion and said second sample portion is divided is in a ratio of 1:1 or 3:1.

5. A mass spectrometer according to claim 1 wherein said first and second fluid splitters are adjustable.

6. A mass spectrometer according to claim 1 wherein said first and second fluid splitters are selected from manual splitters, electronic splitters, and T-splitters.

7. A mass spectrometer according to claim 1 wherein said first sample portion is analyzed in a first ionization mode and said second sample portion is analyzed is a second ionization mode that is different from the first ionization mode.

8. A mass spectrometer according to claim 7 wherein said first and second ionization modes are selected from positive and negative ionization modes.

9. A system for analyzing a liquid sample, comprising:
   (A) a separatory column adapted to receive the liquid sample and separate the sample into a plurality of analytes whereby selected ones of said analytes to be tested form of an analyte testing stream;
   (B) a first fluid splitter adapted to divide said analyte testing stream into a first testing portion and a second testing portion;
   (C) a mass spectrometric apparatus operative to measure physical properties of said analytes in said first and second testing portions;
   (D) a plurality of fluid pathways in communication with said mass spectrometric apparatus, including:
      (1) a first fluid pathway having a first construction and adapted to transfer said first testing portion to said mass spectrometric apparatus in a first time period; and
      (2) a second fluid pathway having a second construction that is different than the first construction and adapted to transfer said second testing portion to said mass spectrometric apparatus in a second time period that is greater than the first time period; and (E) a second fluid splitter interconnecting said first and second fluid pathways at a location downstream of said first fluid splitter and proximate to said mass spectrometric apparatus.

10. A system according to claim 9 wherein said mass spectrometric apparatus is operative to analyze the first testing portion and the second testing portion of said analyte testing stream in either a positive or negative ionization mode.

11. A system according to claim 9 including a computer associated with said separatory column and said mass spectrometric apparatus and operative to generate mass spectral data.

12. A system according to claim 9 wherein said analyte testing stream includes coeluting analytes.

13. A system according to claim 9 wherein said separatory column is a liquid chromatograph.

14. A system according to claim 9 wherein said plurality of fluid pathways are formed of tubing.

15. A system according to claim 14 wherein said tubing has a common diameter for each of said fluid pathways.

16. A method of analyzing a sample containing coeluting analytes with a mass analysis apparatus wherein the mass analysis apparatus has an inlet port communicating therewith to receive the sample for analysis, comprising the steps of:
(A) dividing the sample into a first testing portion and a second testing portion;
(B) directing the first testing portion through a first fluid pathway in communication with the inlet port of the mass analysis apparatus in a first time period and operating the mass analysis apparatus in a first ionization mode thereby to produce a first peak profile;
(C) directing the second testing portion through a second fluid pathway in communication with the inlet port of the mass analysis apparatus in a second time period that is greater than the first time period and operating the mass analysis apparatus in a second ionization mode thereby to produce a second peak profile; and
(D) including a fluid splitter adapted to interconnect said first and second fluid paths and separately direct the first and second testing portions to a third fluid pathway located upstream and proximate to the inlet port of the mass analysis apparatus;
wherein a second fluid splitter is interconnected to said first and second fluid paths thereby dividing said sample into said first and second portions.

17. A method according to claim 16 including the step of simultaneously directing said first and second testing portions through said respective first and second flow paths.

18. A method according to claim 16 including the step of providing a separatory column at a location upstream from the mass analysis apparatus and directing the sample through said separatory column thereby to separate the sample into a plurality of analytes.

19. A method according to claim 16 wherein said first fluid path has a first length and said second fluid path has a second length that is greater than the first length.

20. A method according to claim 16 including the step of changing the mass analysis apparatus from said first ionization mode to said second ionization mode before said second testing portion is received by the inlet port.

* * * * *